United States Patent [19]

Meresz et al.

[11] 4,065,978
[45] Jan. 3, 1978

[54] SYNCHRONIZED DRIVE AND CABLE HANDLING SYSTEM FOR A ROTATIONAL MACHINE ELEMENT

[75] Inventors: Henry Meresz, Wheeling; Michael N. Tranquilla, Elmhurst, both of Ill.

[73] Assignee: G. D. Searle & Co., Skokie, Ill.

[21] Appl. No.: 720,564

[22] Filed: Sept. 7, 1976

[51] Int. Cl.² ............................................. F16C 1/02
[52] U.S. Cl. ..................................................... 74/82
[58] Field of Search ..................... 74/89.2, 82, 217 R

[56] References Cited

U.S. PATENT DOCUMENTS

| | | | |
|---|---|---|---|
| 2,270,485 | 1/1942 | Waters | 74/217 R |
| 2,520,527 | 8/1950 | Campion, Sr. | 74/82 |
| 2,650,093 | 8/1953 | Sheilds | 74/82 |
| 2,797,585 | 7/1957 | Bade | 74/217 R |
| 3,712,147 | 1/1973 | Bernstein | 74/89.2 |

*Primary Examiner*—Benjamin W. Wyche
*Assistant Examiner*—Wesley S. Ratliff, Jr.
*Attorney, Agent, or Firm*—Walter C. Ramm; Dennis O. Kraft; Albert Tockman

[57] ABSTRACT

A synchronized drive and cable handling system is disclosed for a rotational element, such as a rotational gantry of a tomographic scanning machine, upon which element are carried load devices to which a medium, such as oil or electricity, is required to be supplied through the cables. A pair of spaced-apart sets of idler pulleys are disposed to either side of the rotational element with a cable being wound about the respective pulley sets to form an elongated loop, one end of each respective cable being attached to a load device which is disposed on the rotational element. One pulley set of each pair of sets is disposed about a translatable axis, the position of which is controlled by a lead screw drive to vary the distance between the pair of pulley sets and to thus vary the amount of cable which is played-out and taken-in therefrom. A single drive means is provided for effecting rotation of the rotational element and the load devices carried thereon, and for also simultaneously effecting movement of the translatable pulley axes of the cable handling system so that at each side of the rotational element, measured lengths of cable are played-out and taken-in with respect to the rotational element and in synchronism with the rotation of the rotational element, whereby the cables are smoothly and reliably fed during operation, and whereby the inertia of the rotational element remains relatively constant.

12 Claims, 1 Drawing Figure

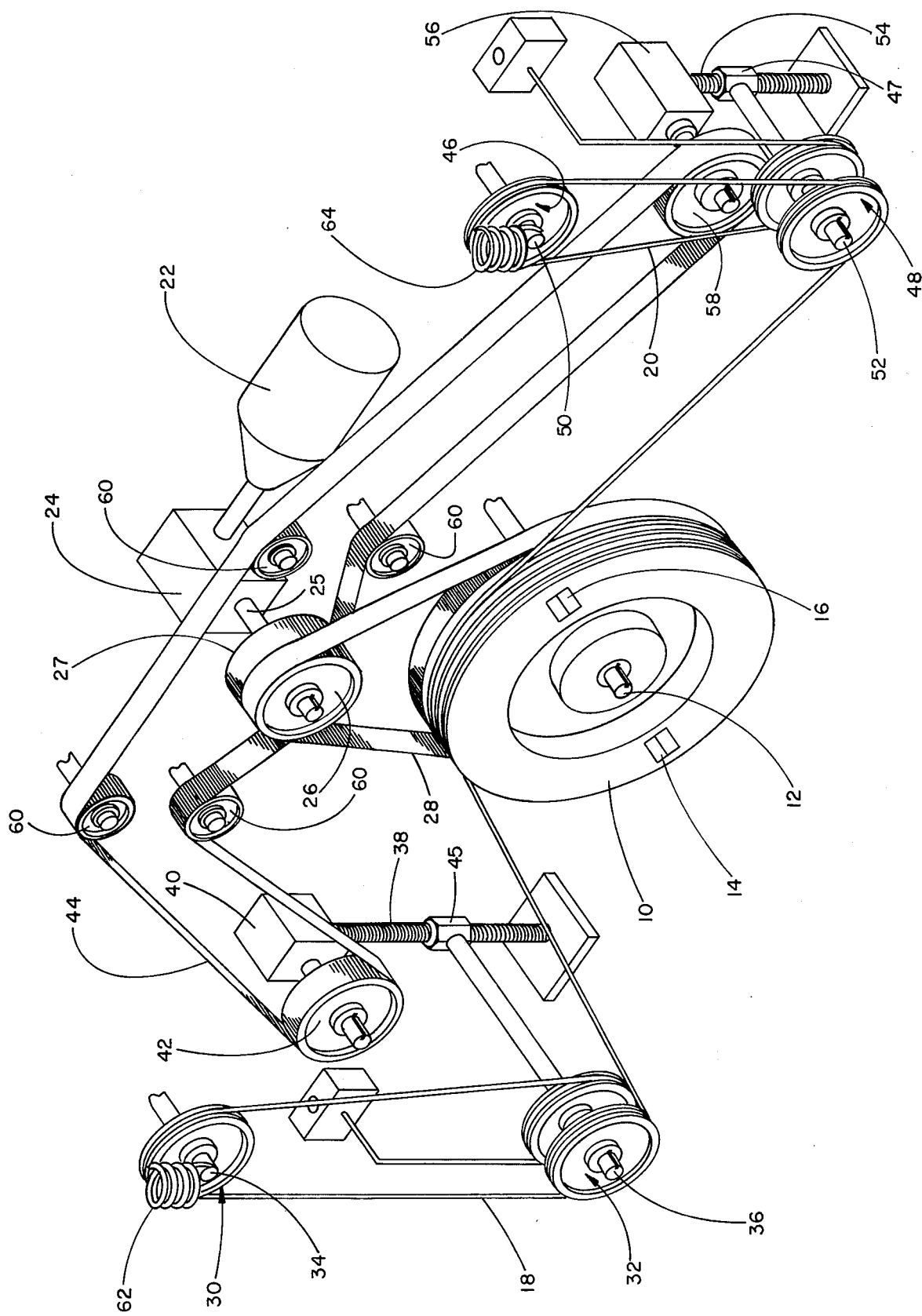

SYNCHRONIZED DRIVE AND CABLE HANDLING SYSTEM FOR A ROTATIONAL MACHINE ELEMENT

BACKGROUND OF THE INVENTION

This invention broadly relates to cable or conduit handling devices and is specifically directed to the provision of a synchronized drive and cable handling system for a rotational machine element, upon which element are carried load devices to which a medium is required to be supplied through the cables, all to the end that measured lengths of cable are played-out and taken-in in synchronism with the rotation of the rotational element.

Many machine systems utilize rotational elements or rotors which carry devices to which a medium is required to be supplied through cables. For example, and with particular reference to computerized tomographic X-ray apparatus, a rotatable circular gantry is often times provided, which rotatable gantry carries an X-ray tube as well as a plurality of X-ray detectors. With such an arrangement, it is necessary to feed power to the tube, to send and receive signal information from the detectors, and perhaps additionally to supply a cooling flow of oil for the X-ray tube.

The necessity to supply such mediums to such devices which are carried by the rotational machine element such as the rotatable gantry poses significant problems. Specifically, and if such mediums are to be externally supplied by means of a cable or conduit attached at one end to the devices per se, some technique is necessary so that the cables can be played-out and taken-in with respect to the rotational element during the rotation thereof so that the cables do not become tangled, placed under undue stress and tension, and the like.

A further requirement of such a cable handling system in the contemplated environments of utility is that such system must of necessity operate in substantial synchronism with the rotation of the rotatable element. To achieve such synchronous operation, and to do so at a relatively low manufacturing cost by which the necessity of complex electronic synchronizing components is eliminated as is the resultant unreliability thereof, is a significant task.

BRIEF SUMMARY OF THE INVENTION

It is the primary objective of the instant invention to provide, in this contemplated environment of utility, a cable handling system which is capable of smoothly and reliably feeding cables or conduits at a substantially constant tension during rotation of a rotational element to which the cables are attached, all in substantial synchronism with the rotational movement of the rotational element.

It is a further objective of the instant invention to provide an improved cable handling system of the type described which achieves its synchronous operation in a simple and reliable mechanical fashion.

Yet another objective of the instant invention is the provision of an improved synchronized drive and cable handling system for a rotational element carrying devices to which a medium is required to be supplied through the cables, which system requires low manufacturing cost and which system results in a compact construction.

Still another objective is to provide such a cable handling system which, during operation thereof, assures that the weight and thus the inertia of the rotational element is maintained substantially constant throughout its rotation.

These as well as other objectives are implemented by the instant invention which, as aforementioned, is directed to the provision of an improved synchronized drive and cable handling system for a machine of the type which incorporates a driven rotational element, which element carries devices to which a medium is required to be supplied through the cables. In the preferred embodiment, the cable handling mechanism of the invention comprises at least first and second spaced apart sets of idler pulleys about which sets the cable is wound to form an elongated loop, with one end of the cable being attached to the device carried by the rotational element, and with the other end of the cable terminating externally thereof, to which other end a source of supply, for example, of any desired medium would be connected. The elongated loop, therefore, is formed intermediate the cable ends.

Means are provided to effect variation in the length of the elongated loop during operation of the apparatus. Specifically, one pulley set is preferably disposed about a first substantially fixed axis, whereas the second pulley set is preferably disposed about a translatable axis. When the translatable axis is moved or translated, the distance between the first and second axis is varied as is the length of the elongated loop. By so varying the length of the elongated loop, the cable can be played-out and taken-in with respect to the rotational element.

Importantly, the taking-in and playing-out of the cable takes place in substantial synchronism with the rotation of the rotatable element so as not to place the cables under unnecessary stress or tension. To this end, a single drive means is contemplated for causing rotation of the rotatable element and for further effecting synchronous operation of the pulley arrangement so as to carefully control the translation of the second axis to thus take-in or play-out measured lengths of cable.

In the contemplated preferred embodiment, the mechanism by which the second axis of the pulley arrangement is translated includes a lead screw arrangement with the second axis being mounted upon a nut mechanism disposed about the lead screw. The lead screw is itself rotated by means of a gear box which incorporates a driven pulley. A flexible belt or chain is connected to the driven pulley of the lead screw gear box and is further disposed about the same single drive means which serves to effect rotation of the rotatable element. Thus, substantial synchronism between the action of the cable handling mechanism and the rotation of the rotatable element is assured.

Where a plurality of cable handling mechanisms are desired, further pulley arrangements can be disposed to opposite sides of the rotatable element, each pulley arrangement being similar in construction with one exception. Specifically, the lead screw mechanism to one side of the rotatable element would incorporate right-hand threads, whereas the lead screw mechanism to the other side of the rotatable element would incorporate left-hand threads. Each lead screw mechanism could be driven by a single shared or common synchronizing belt disposed about the single drive means for the rotatable element, or individual belts coupled to the single drive. Thus, as one cable handling mechanism played-out a measured length of cable during rotation of the rotatable element, the other cable handling mechanism would take-in the same measured length of its own cable.

BRIEF DESCRIPTION OF THE DRAWINGS

The invention itself will be better understood and further features and advantages thereof will become apparent from the following detailed description of a preferred inventive embodiment, such description making reference to the single appended sheet of drawings in which the sole FIGURE thereof is a perspective illustration of one form of the invention.

DETAILED DESCRIPTION OF THE INVENTION

With reference now to the appended sheet of drawings, a rotational element 10 is shown as being mounted for rotation about a central axis 12, the rotational element 10 carrying devices, such as load devices 14 and 16, to which a medium, such as electric power, hydraulic fluid and/or the like, is required to be supplied through cables 18 and 20 attached at one end thereto, each of the respective cables terminating externally of the rotational element 10 as shown.

The rotational element 10 is contemplated to be driven by means of an electric motor 22 coupled through a gear box 24 having an output shaft 25 to which is connected a drive pulley 26 about which a non-slip flexible belt, chain or the like 28 is disposed. As is clearly indicated, upon rotation of the drive pulley 26, such rotational motion will be transferred to rotational element 10 by means of flexible belt 28. In the preferred environment of utility of the invention, the rotational element 10 would rotate through at least 360°, for example, in one direction. Then, and through non-illustrated conventional motor controls, the direction of rotation would be reversed so as to bring the rotational element 10 back into its original or starting position.

The cable handling system of the instant invention contemplates the provision on one side of the rotational element 10 of first and second spaced-apart idler pulley sets 30 and 32, respectively, with the first pulley set 30 being disposed about a first axis 34, and with the second pulley set being disposed about a second axis 36, the structural features of which will be discussed hereinbelow. Pulley set 30 comprises a single pulley in this example, whereas pulley set 32 includes two co-axially mounted though independently rotatable pulleys as illustrated. The specific number of pulleys provided in each set is not critical and can be varied to adjust the feeding characteristics and parameters of the system. As between sets, the number of pulleys provided will differ by one.

Cable 18 is wound about the separate pulleys of the first and second spaced-apart pulley sets 30 and 32 to form the illustrated elongated loop, one end of cable 18 being attached to load device 14 of the rotational element 10, and with the other end of the cable 18 being clamped and terminating externally, such that the elongated loop is consequently formed intermediate the cable ends.

Translating means are provided so as to vary the distance between the first and second axes 34 and 36, respectively, and thus vary the length of the elongated cable loop. In this fashion, the cable 18 can be played-out and taken-in with respect to the rotational element 10. In the preferred embodiment as is illustrated, the first axis 34 is substantially fixed in position, whereas the second axis 36 is translatable. The translating means in this instance would therefor effect translation of the second axis 36 and comprises a lead screw 38, a gear box means 40 including a driven pulley 42 for rotating the lead screw, and a lead screw nut mechanism 45 upon which the second axis 36 is mounted. Upon rotation of the driven pulley 42, the lead screw is rotated and the lead screw nut mechanism 45 is caused to translate either upwardly or downwardly about the lead screw axis so as to effect a variance in the distance between the first and second idler pulley sets 30 and 32 respectively.

As mentioned at the outset, it is of importance that the cable 18 be played-out and/or taken-in with respect to the rotational element 10 in synchronism with the rotation thereof. To effect such synchronism, the same drive shaft 25 which provides the output from the electric motor 22 and which serves to effect the rotation of the rotational element 10 by means of drive pulley 26 is caused to additionally effect rotation of the driven pulley 42 of the gear box means 40 for lead screw 38 by means of an additional drive pulley 27 similarly coupled to the shaft. Specifically, and in the preferred embodiment as illustrated, a second non-slip flexible belt, chain or the like 44 is disposed about the drive pulley 27 of the drive means for the rotational element 10, and the driven pulley 42 of the lead screw gear box means 40. With the elements as above-described, when rotational element 10 rotates clockwise in the direction of the arrows due to a clockwise rotation of the drive pulley 26 coupled to the rotational element 10 through the flexible belt 28, a clockwise rotation of the driven pulley 42 of the lead screw gear box means 40 will similarly be effected through the second flexible belt 44. Assuming, in this instance, that lead screw 38 contains so-called "left-hand" threads, the translatable axis 36 and thus the second pulley set 32 will move upwardly towards the idler pulley set 30, thus shortening the length of the elongated loop of cable 18 and playing-out a measured length of such cable, which measured length would consequently wrap about the rotational element 10 as the element turns.

To increase the cable-handling capacity of the instant invention, it is possible, of course, to provide a plurality of cables such as cable 18 disposed about the first and second pulley sets 30 and 32, respectively. Either additional grooves could be provided in each of the individual idler pulleys of each set to accommodate the extra cables, or alternatively, a number of extra separate idler pulleys could be disposed about the respective axes. The only requirement, of course, is that each such cable provided be of approximately the same cable diameter so that the same measured length of cable will be played-out or taken-in during operation of the cable handling mechanism. Simply increasing the number of cables disposed about the pulley sets, however, is not the most advantageous solution to the problem of increasing the cable handling capacity of the mechanism, in that a rather bulky arrangement would result. To overcome this disadvantage, the invention contemplates the provision of an additional cable handling mechanism disposed to the opposite side of the rotational element 10 as shown.

In this respect, it is to be noted that third and fourth spaced-apart idler pulley sets 46 and 48 are provided about which a further cable 20 is wound to form a second elongated loop, with one end of cable 20 being attached to load device 16 of rotational element 10 as has already been described, and with the other end of cable 20 being clamped and terminating externally such that a second elongated loop is formed intermediate the cable ends.

In a fashion similar to the construction of the first cable handler mechanism constituting pulley sets 30 and 32, the third pulley set 46 can be disposed about a third substantially fixed axis 50, while the fourth pulley set 48 can be disposed about a translatable fourth axis 52. Further translating means are again similarly provided for effecting translation of the fourth axis 52 such that the distance between the third and fourth axes and thus the length of the second elongated loop is variable.

To this end, an additional lead screw 54 is provided which is rotationally driven by a gear box means 56 which includes a driven pulley 58. The translatable fourth axis 52 is again mounted upon a lead screw nut mechanism 47 such that, upon rotation of the lead screw 54, the lead screw nut mechanism 47 and thus the axis 52 mounted thereon moves in a direction either towards or away from the third substantially fixed axis 50 and the idler pulley set 46 carried thereby. In contrast with the construction of the first cable handling mechanism, lead screw 54 is contemplated to contain so-called "right-hand" threads such that, upon rotation of the driven pulley 58 in the same direction as driven pulley 42 of the first cable handling mechanism, the translatable fourth axis 52 and thus the fourth idler pulley set 48 will move downwardly, i.e., away from the third idler pulley set 46, so as to lengthen the elongated loop of cable 20 and thus take-in such cable with respect to rotational element 10.

Driven pulley 58 of the lead screw gear box means 56 is preferably placed into motion by the same flexible belt 44 which is disposed about the driven pulley 42 of the lead screw gear box means 40, flexible belt 44 being run upon guiding idler pulleys 60 as shown, the placement and mounting of the idler pulleys 60 being adjustable by any suitable though non-illustrated mechanism such that the flexible belt 44 of necessity is placed under pressure in a partially wrapped condition on the drive pulley 27 of the electric motor 22, so that a non-slip running connection is made therebetween. Alternatively, an additional belt could be provided between another non-illustrated drive pulley on the common drive shaft 25, and the driven pulley 58.

By utilizing a common drive shaft 25 whose rotation is transmitted so as to simultaneously drive both cable handling mechanisms as illustrated, synchronism between each cable handling mechanism is assured. Further, and as already has been appreciated, by utilizing a single drive shaft 25 to effect not only rotation of the rotational element 10 but to also drive the cable handling mechanisms, synchronism between the playing-out and taking-in of the respective cables in conjunction with the rotation of the rotational element 10 is brought about.

Lastly, the instant invention further takes into consideration the possibility of a slight stretching of the respective cables 18 and 20, which stretching might alter the tension under which the respective cables are maintained and thus alter or vary the measured length of cable that is played-out or taken-in. To compensate for any such stretching of the respective cables, it is to be appreciated that the first axis 34 as well as the third axis 50 of each respective cable handling mechanism is biased by resilient spring arrangements 62 and 64, respectively, in a direction away from the second and fourth axes 36 and 52, respectively, so as to maintain the respective cables under proper tension at all times. Additionally, this resilient mounting arrangement serves to compensate for tolerance variations in the system construction and allows the cable handling apparatus sufficient flexibility to continue to properly play-out cable when the rotational element is rotated somewhat beyond 360° in one direction.

It should now be recognized that the objectives set forth at the outset of this specification have been successfully achieved. Accordingly,

What is claimed is:

1. In a machine of the type incorporating a driven rotational element, upon which element are carried devices to which a medium is required to be supplied through cables attached at one end thereto, the other end of said cables terminating externally of the rotational element, an improved synchronized drive and cable handling system for the rotational element by which the cables are smoothly and reliably fed and wound thereon at a substantially constant tension during rotation of the element, said improvement comprising: a plurality of pulleys grouped into first and second spaced-apart idler pulley sets, the number of pulleys in each said set differing by one, and about which pulley sets a cable is wound to form an elongated loop intermediate the cable ends with one end of the cable extending from said loop and being attached to a device carried by the rotational element, and with the other end of the cable extending from said loop and terminating externally of the rotational element; all pulleys of said first pulley set being disposed about a first axis; all pulleys of said second pulley set being disposed about a second axis; translating means for varying the distance between said first and second axes and thus varying the length of said elongated loop, whereby the cable can be played-out and taken-in with respect to the rotational element; a drive means for causing rotation of the rotational element; and means for controlling the operation of said translating means such that said translating means respectively plays-out and takes-in measured lengths of cable in synchronism with the speed and direction of rotation of the rotational element.

2. The improvement defined in claim 1, wherein said means for controlling the operation of said translating means such that said translating means plays-out and takes-in measured lengths of cable in synchronism with the rotation of the rotational element comprises a mechanical coupling disposed between said drive means and said translating means whereby said drive means causes rotation of the rotational element as well as operation of said translating means.

3. The improvement defined in claim 2, wherein said drive means comprises a pulley driven by the shaft of an electric motor, a first belt being disposed about said drive pulley and the rotational element to effect rotation thereof; and wherein said mechanical coupling comprises a second belt driven by said shaft of said electric motor and coupled to said translating means.

4. The improvement defined in claim 3, wherein said first axis is substantially fixed, and wherein said second axis is translatable, said translating means effecting translation of said second axis so as to vary the distance between said first and second axes.

5. The improvement defined in claim 1, further including an additional plurality of pulleys grouped into third and fourth spaced-apart idler pulley sets, the number of pulleys in each said set differing by one and about which pulley sets a further cable is wound to form a second elongated loop with one end of the further cable extending from said second loop and being attached to a device carried by the rotational element, and with the other end of the further cable extending from said second loop and terminating externally of the rotational element; said second elongated loop being formed intermediate the further cable ends; said third and fourth pulley sets and said second elongated loop formed thereat being on a side of the rotational element opposite the location of said first and second pulley sets and said elongated loop formed thereat; all pulleys of said third pulley set being disposed about a third axis; all pulleys of said fourth pulley set being disposed about a fourth axis; further translating means for varying the distance between said third and fourth axes and thus the length of said second elongated loop in a manner equal and opposite to the variation of the length of said first elongated loop, whereby the further cable can be played-out and taken-in with respect to the rotational element; and wherein said means for controlling the operation of said first mentioned translating means additionally controls the operation of said further translating means whereby said further translating means takes-in the further cable when said first-mentioned translating means plays-out the first-mentioned cable.

6. The improvement defined in claim 5, wherein said means for controlling the operation of each of said translating means such that each said translating means plays-out and takes-in measured lengths of cable in synchronism with the rotation of the rotational element comprises a mechanical coupling disposed between said drive means and each said translating means whereby said drive means causes rotation of the rotational element as well as operation of each said translating means.

7. The improvement defined in claim 6, wherein said drive means comprises a pulley driven by the shaft of an electric motor, a first belt being disposed about said drive pulley and the rotational element to effect rotation thereof; and wherein said mechanical coupling means comprises at least one additional belt driven by said shaft of said electric motor coupled to both said first-mentioned and further translating means.

8. The improvement defined in claim 7, wherein said first axis of said first pulley set and said third axis of said third pulley set is substantially fixed, and wherein said second axis of said second pulley set and said fourth axis of said fourth pulley set is translatable, each said translating means effecting translation of said respective second and fourth axes so as to respectively vary the distance between said first and second axes, and said third and fourth axes.

9. The improvement defined in claim 8, wherein each said translating means comprises a lead screw, gear box means including a driven pulley for rotating said lead screw, and a lead screw nut mechanism upon which said second and fourth axes are respectively mounted; and wherein said at least one additional belt is disposed about a drive pulley driven by said shaft of said electric motor and said driven pulley of each said lead screw gear box means, the lead screws of each respective translating means being oppositely threaded.

10. The improvement defined in claim 9, further including means for biasing said first and third axes in a direction away from said second and fourth axes, respectively, so as to maintain the respective cables under tension.

11. In a machine of the type incorporating a driven rotational element, upon which element are carried devices to which a medium is required to be supplied through cables attached thereto, which cables terminate externally of the rotational element, an improved synchronized drive and cable handling system for the rotational element by which the cables are smoothly and reliably fed at a substantially constant tension during rotation of the element, said improvement comprising: first and second spaced-apart idler pulley sets about which a cable is wound to form an elongated loop with one end of the cable being attached to a device carried by the rotational element, and with the other end of the cable terminating externally thereof, said elongated loop being formed intermediate the cable ends; said first pulley set being disposed about a substantially fixed first axis; said second pulley set being disposed about a translatable second axis mounted on a lead screw nut mechanism; translating means comprising a lead screw upon which said nut mechanism is disposed and a driven pulley operated gear box means for rotating said lead screw and effecting translation of said second axis so as to vary the distance between said first and second axes and thus vary the length of said elongated loop, whereby the cable can be played-out and taken-in with respect to the rotational element; a drive means having a motor shaft drive pulley of about which drive pulley and said rotational element a first belt is disposed for causing rotation of the rotational element; and a second belt disposed about a drive pulley of said motor shaft and said driven pulley of said lead screw gear box means such that said translating means plays-out and takes-in measured lengths of cable in synchronism with the rotation of the rotational element.

12. The improvement defined in claim 11, further including means for biasing said first axis in a direction away from said second axis so as to maintain the cable under tension.

* * * * *

Disclaimer 4,065,978.—*Henry Meresz*, Wheeling, and *Michael N. Tranquilla*, Elmhurst, Ill. SYNCHRONIZED DRIVE AND CABLE HANDLING SYSTEM FOR A ROTATIONAL MACHINE ELEMENT. Patent dated Jan. 3, 1978. Disclaimer filed June 19, 1978, by the assignee, *G. D. Searle & Co.*

Hereby enters this disclaimer to all claims of said patent.

[*Official Gazette September 5, 1978.*]